US009867767B2

(12) United States Patent
Klein et al.

(10) Patent No.: US 9,867,767 B2
(45) Date of Patent: Jan. 16, 2018

(54) USE OF GLUCOSYLGLYCEROL

(75) Inventors: Julia Klein, Bochum (DE); Gerhard Stumm, Hamburg (DE)

(73) Assignee: Bitop AG, Witten (DE)

( * ) Notice: Subject to any disclaimer, the term of this patent is extended or adjusted under 35 U.S.C. 154(b) by 0 days.

(21) Appl. No.: 13/060,122

(22) PCT Filed: Aug. 21, 2009

(86) PCT No.: PCT/EP2009/006083
§ 371 (c)(1),
(2), (4) Date: Apr. 27, 2011

(87) PCT Pub. No.: WO2010/020424
PCT Pub. Date: Feb. 25, 2010

(65) Prior Publication Data
US 2011/0207681 A1 Aug. 25, 2011

(30) Foreign Application Priority Data
Aug. 22, 2008 (DE) ........................ 10 2008 039 231

(51) Int. Cl.
A61K 31/7032 (2006.01)
A61P 17/00 (2006.01)
A61P 39/06 (2006.01)
A61K 8/60 (2006.01)
A61Q 19/00 (2006.01)

(52) U.S. Cl.
CPC .............. A61K 8/602 (2013.01); A61Q 19/00 (2013.01); A61K 2800/78 (2013.01)

(58) Field of Classification Search
CPC ..... A61K 8/602; A61K 2800/78; A61Q 19/00
USPC ......................................................... 514/25
See application file for complete search history.

(56) References Cited

U.S. PATENT DOCUMENTS

| | | | |
|---|---|---|---|
| 4,261,995 A | 4/1981 | Weinhardt et al. | |
| 4,668,513 A | 5/1987 | Reichert | |
| 4,871,545 A | 10/1989 | Dethlefsen | |
| 5,376,365 A | 12/1994 | Dikstein | |
| 5,789,414 A | 8/1998 | Lapidot et al. | |
| 5,834,473 A | 11/1998 | Virtanen et al. | |
| 5,891,854 A * | 4/1999 | Thiem et al. ................... | 514/25 |
| 6,060,071 A | 5/2000 | Motitschke et al. | |
| 6,080,401 A | 6/2000 | Reddy et al. | |
| 6,267,973 B1 | 7/2001 | Motitschke et al. | |
| 6,403,112 B2 | 6/2002 | Motitschke et al. | |
| 6,485,711 B1 | 11/2002 | Olmstead | |
| 6,602,514 B1 | 8/2003 | Bunger et al. | |
| 6,716,819 B2 | 4/2004 | Welsh et al. | |
| 7,048,910 B2 | 5/2006 | Buenger et al. | |
| 7,147,849 B2 | 12/2006 | Barth et al. | |
| 7,714,011 B2 | 5/2010 | Clarot et al. | |
| 8,765,691 B2 | 7/2014 | Krutmann et al. | |
| 8,822,477 B2 | 9/2014 | Krutmann | |
| 9,089,568 B2 | 7/2015 | Schwarz et al. | |
| 2001/0056068 A1 | 12/2001 | Chwalisz et al. | |
| 2002/0151541 A1 | 10/2002 | Pairet et al. | |
| 2003/0021817 A1 | 1/2003 | Arnaud-Sebillotte et al. | |
| 2003/0054021 A1 | 3/2003 | Dalko et al. | |
| 2003/0147818 A1 | 8/2003 | Dubief et al. | |
| 2003/0147937 A1 | 8/2003 | Schwartz | |
| 2004/0028631 A1 | 2/2004 | Schwartz | |
| 2004/0053860 A1 | 3/2004 | Buchholz et al. | |
| 2004/0071691 A1 | 4/2004 | Barth | |
| 2004/0220137 A1 | 11/2004 | Sauermann | |
| 2006/0188496 A1 | 8/2006 | Bentz et al. | |
| 2006/0246007 A1 | 11/2006 | Krutmann | |
| 2007/0122464 A1 | 5/2007 | Krutmann | |
| 2007/0166238 A1 | 7/2007 | Duggan et al. | |
| 2008/0014153 A1 | 1/2008 | Schwartz | |
| 2009/0060876 A1 | 3/2009 | Schwartz | |
| 2009/0130223 A1 * | 5/2009 | Breitenbach ........... | A61K 8/602 424/606 |
| 2009/0318372 A1 * | 12/2009 | Godl et al. ..................... | 514/25 |
| 2010/0048900 A1 | 2/2010 | Schwartz | |
| 2010/0297034 A1 | 11/2010 | Schmittmann | |
| 2011/0053896 A1 | 3/2011 | Krutmann et al. | |
| 2011/0152294 A1 | 6/2011 | Krutmann | |
| 2011/0207681 A1 | 8/2011 | Klein | |
| 2011/0306568 A1 | 12/2011 | Schwarz et al. | |

(Continued)

FOREIGN PATENT DOCUMENTS

| | | | |
|---|---|---|---|
| EP | 0816509 A3 | | 11/1999 |
| JP | 2004331583 | * | 11/2004 |
| JP | 2008-024622 | | 2/2008 |

(Continued)

OTHER PUBLICATIONS

Smith et al. Gene expression profiling of skin carcinogenesis in mice using cDNA microarrays. CEFIC-Long Range Initiative Report 9, pp. 1-6, Apr. 2005.*
Klaus Unfried, et al.; U.S. Appl. No. 14/323,017, filed Mar. 5, 2014.
Notice of Allowance issued May 6, 2014 in U.S. Appl. No. 10/563,586, filed Dec. 13, 2006.
Notice of Allowance issued Feb. 20, 2014 in U.S. Appl. No. 12/675,264, filed Oct. 5, 2010.
Notice of Allowance issued Mar. 30, 2015 U.S. Appl. No. 11/885,687, filed Apr. 16, 2008.
Volkov, V.T.,Tubercle and Lung Disease, Oct. 1995, 76(1 ), p. 59.
Shima et al, Activation and thermostabilization effects of cyclic 2,3-diphosphoglycerate on enzymes from the hyperihermophilic Methanopyrus kandleri, Arch. Microbial. 1998, 170, 469-72.
Buommino, E., et al, Ectoine from halophilic microorganisms induces the expression of hsp70 and hsp70B in human keratinocytes modulating the proinflammatory response, Cell Stress & Chaperones, 10(3):197-203. 2005.

(Continued)

Primary Examiner — Yih-Horng Shiao
(74) Attorney, Agent, or Firm — Berliner & Associates

(57) ABSTRACT

The invention relates to the use of glucosylglycerol or glucosylglycerol esters with a view to increasing the expression of cell protective enzymes for the protection and stabilization of human skin and/or mucous membranes. It has been demonstrated that glucosylglycerol plays an effective role in the stimulation and activation of cell protective enzymes such as superoxide dismutase. It is thus possible in this manner to protect human skin cells effectively against damaging external influences.

9 Claims, No Drawings

(56) References Cited

U.S. PATENT DOCUMENTS

2013/0085149 A1    4/2013  Schmittmann
2014/0315869 A1    10/2014  Unfried et al.

FOREIGN PATENT DOCUMENTS

| WO | 9200744 A1 | 1/1992 |
| WO | 9217170 A1 | 10/1992 |
| WO | 0036915 A1 | 6/2000 |
| WO | 2005002556 A1 | 1/2005 |
| WO | 2005002581 A1 | 1/2005 |
| WO | 2006097263 A2 | 9/2006 |
| WO | 2009056292 A1 | 5/2009 |

OTHER PUBLICATIONS

Hanifin, JM, et al, Effects of a Low-potency Corticosteroid Lotion Pius a Moisturizing Regimen in the Treatment of Atopic Dermatitis, Current Therapeutic Research, vol. 59, No. 4, Apr. 1998, p. 227-233.
Loden, M., et al, Improvement in skin barrier function in patients with atopic dermatitis after treatment with a moisturizing cream (Canoderm®), British Journal of Dermatology, 1999: 140: p. 264-267.
Derwent publication for DE10044985, of Buenger et al, (2001).
Machine translation of DE10044985 of Buenger et al. (2001).

* cited by examiner

USE OF GLUCOSYLGLYCEROL

The invention relates to the use of glucosylglycerol within the framework of cosmetic or dermatological preparations.

DE 195 40 749 A1 describes the use of glycosyl glycerides in cosmetic and dermatological preparations. Substances of this nature can be put to use as so-called moisturizers, that is as substances having moisture-adding properties. Especially preferred here is the use of 2-O-β-D-glucosylglycerol.

Glucosylglycerol, or more specific 2-O-α-D-glucosylglycerol, is a natural substance synthetized, for example, from cyanobacteria which make use of its properties for osmoprotective purposes. In this manner cyanobacteria are capable of growing in saline media with concentrations of up to 1.5 M NaCl. The molecule accumulates in high concentrations in the cytoplasm and in this way causes the existing osmotic pressure existing in such an environment due to the high salt concentration to be reduced thus protecting the cell against water losses. An example here is the cyanobacterium *Synechocystis* sp. PCC 6803.

Furthermore, the molecule is also synthetized by plants of genus *myrothamnus*. These plants are growing in humid-to-dry environments. *Myrothamnus flabellifolia* is a small shrub found in the southern region of Africa growing on rock slabs up to a height of 60 cm. The plant survives completely unharmed and in desiccated condition drought periods occurring in the southern African region and lasting several months. However, as soon as it rains again the plant begins to sprout within a few hours so that it is also known under the byword of "resurrection plant". The structure of 2-O-α-D-glucosylglycerol is as follows:

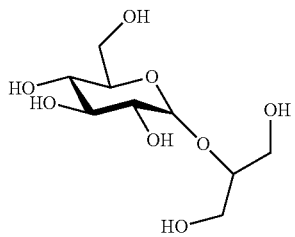

Surprisingly, it has now been found and ascertained through tests conducted with human skin cells that glucosylglycerols are capable of increasing the expression of cell protective enzymes. Therefore, the invention relates to the use of glucosylglycerol with a view to increasing the expression of cell protective enzymes for the protection and stabilization of human skin and/or mucous membranes.

The efficiency of glucosylglycerol could be proved based on tests conducted with keratinocytes and fibroblasts. In these tests appropriate cell cultures were treated with a glucosylglycerol solution and the transcribed mRNA quantified. For this purpose the mRNA was first extracted to produce a $^{33}$P labeled target with the help of a reverse transcriptase. Following this, these targets were applied to a cDNA chip and the radioactivity measured by means of the phosphor imaging method. The cDNA chip contained an array of the cDNAs of various proteins.

It has been found in this context that the expression of cell protection enzymes is upregulated. Cell protection enzymes are in particular those that are capable of decomposing reactive oxygen compounds. An example here is the superoxide dismutase which is an enzyme that protects eukaryotic cells against reactive superoxide ions. In this process the oxidized form of the enzyme reacts with a superoxide anion thus producing oxygen and the reduced form of the enzyme.

This form then reacts with a second superoxide anion giving rise to the formation of hydrogen peroxide and causing a re-formation of the oxidized form of the enzyme. This can expediently be expressed by the following equation:

$$2O_2^- + 2H^+ \rightarrow H_2O_2 + O_2$$

Another important enzyme in this context is the catalase which disproportionates hydrogen peroxide to form oxygen and water. In this manner catalase similar to superoxide dismutase reduces the oxidative stress acting on the skin cells.

Glutathione peroxidase as well plays a significant role in the cellular defense system combatting negative effects of oxidative stress. Glutathione peroxidase catalyzes the glutathione-dependent reduction of organic peroxides and hydrogen peroxide.

The so-called cell protection enzymes which are capable of decomposing reactive oxygen compounds, in particular superoxide anions, hydroxyl radicals and peroxides, play an important part in the protection against oxidative stress. As interface and surface of the human body the skin/mucous membrane is exposed to numerous external stresses. Human skin is an organ that consists of a variety of specialized cell types—keratinocytes, melanocytes, Langerhans cells, Merkel cells and others—and protects the body against external influences. In this context a distinction must be made between physical, chemical and biological factors that may have impact on human skin. Physical influences are, inter alia, thermal and mechanical influences as well as the effects of radiation such as, for example, UV, VIS and IR radiation. Chemical influences particularly involve, inter alia, the exposure to and effects of chemicals, toxins, free radicals, allergens, denaturing substances, substances attaching to DNA and substances damaging or deactivating proteins. Airborne particulate may also have detrimental effects. External biological influences mean the effects caused by foreign organisms and their metabolic products. Human skin may also be affected by thermal influences. According to the present invention the use of glucosylglycerol can protect the skin against influences of the nature described above.

How cell protection enzymes are stimulated and activated could in particular be shown in the case of the superoxide dismutases SOD-1 and SOD-2. Regarding keratinocytes and using a 0.5-% glucosylglycerol solution it was possible to increase the expression of SOD-1 4.7 times within 24 hours, and raise it 19.6 times within 96 hours. As far as SOD-2 was concerned tests with fibroblasts using a 1-% glucosylglycerol solution have shown a 25.4 times higher expression within 24 hours and within 96 hours a 34.4-fold increase could be achieved.

Aside from enzymes decomposing reactive oxygen compounds other cell protection enzymes may also be upregulated, for example DNA repairing enzymes such as ligases. Chaperones represent another class and facilitate the correct folding of proteins.

The glucosylglycerol employed is preferably the naturally occurring 2-O-α-D glucosylglycerol which for example is accumulated by cyanobacteria of genus *Synechocystis*. However, comparable effects can also be expected from the β-glycosidic linkage of glucose to the glycerol molecule or from the linkage of glucose to glycerol at the 1-position. The following glucosylglycerols are thus conceivable, with only the notation of the molecules in the D-configuration being represented here:

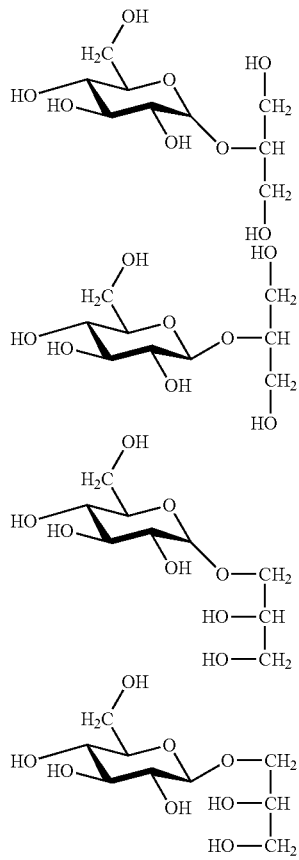

Esters of glucosylglycerol may also be put to use.

The glucosylglycerol may be employed for purposes described hereinbefore in the form of cosmetic, dermatological and pharmaceutical preparations. The concentration may, for example, range between 0.001% w/w and 10% w/w, in particular between 0.01% w/w and 6% w/w in relation to the total weight of the preparation.

In particular, the glucosylglycerol is provided in an aqueous solution. Nevertheless, emulsions and microemulsions of the type water-in-oil (W/O) or of type oil-in-water (O/W) are basically conceivable as well.

Customary cosmetic auxiliary agents may be used, for example carrier substances, preservation agents, bactericides, perfumes, solutizers, vitamins, stabilizers, anti-foaming agents, thickeners, colorants, surfactants, emulsifiers, moisturizers and the like.

The cosmetic or dermatological preparations containing glucosylglycerol are meant to be administered topically. They may, for example, be used in the form of solutions, suspensions, emulsions, pastes, ointments, gels, creams, lotions, powder, soaps, surfactant-containing cleansing preparations, oils, sprays and lipsticks.

Ointments, pastes, creams and gels may contain customary carrier substances such as, for example, animal and vegetable fats, waxes, paraffins, starch, traganth, cellulose derivatives, polyethylene glycols, silicones, bentonites, silicic acid, talcum and zinc oxide or mixtures/blends of these substances.

In addition to the customary carrier substances powders and sprays may contain the customary propellants, e.g. propane/butane or dimethyl ether.

Solutions and emulsions may contain customary carrier substances such as solvents, solutizers and emulsifiers or oils.

Suspensions typically contain additional carrier substances such as water or ethanol.

Glucosylglycerol may be produced in accordance with a method described in WO 2008/034158 A2. In this case a saccharose phosphorylase is allowed to interact with a blend that has a glucosyl donor and glycerol as glucosyl acceptor. Preferably, the glucosyl donor is saccharose.

The increase of the expression of cell protective enzymes could be shown as follows:

The investigations were carried out with epidermal keratinocytes (NHEK, normal human epidermal keratinocytes) and dermal fibroblasts (NHDF, normal human dermal fibroblasts). In the case of the keratinocytes a 0.5-% (w/w) and in the case of the fibroblasts a 1-% (w/w) aqueous glucosylglycerol solution was used for the treatment.

Culture Conditions:
37° C., 5% $CO_2$
Culturing Medium:
Keratinocytes: Keratinocyte-SFM (Invitrogen 17005-034) blended with epidermal growth factor (EGF) 0.25 ng/ml, pituitary extract (PE) 25 µg/ml (Invitrogen 3700015), Gentamycin 25 µm/ml (Sigma G1397)
Fibroblasts: DMEM (Invitrogen 21969035), blended with L-glutamine 2 mM (Invitrogen 25030024), Penicillin 50 UI/ml/Streptomycin 50 µg/ml (Invitrogen 15070063), fetal calf serum 10% (FCS, Invitrogen 10270098)

Culturing took place for a period of 24 and 96 hours. At the end of the incubation period the cells were washed with PBS solution (Invitrogen 14190094).

The extraction of mRNA of each culture was achieved using Tri Reagent as per a standard protocol. The relevant cDNAs with $^{33}$P-labeled targets was produced by reverse transcription of mRNA using [$\alpha^{33}$P]-dATP and oligodT.

The labeled cDNA targets were hybridized to the specific cDNA probes covalently fixed to minichips. After thorough washing the relative amount of the hybridized targets was determined by means of the phosphor imaging method. This analysis was performed by measuring the radioactivity by means of a "Cyclone" Phosphor Imager (Packard Instruments; 72 hours exposure time) and using the ImageQuant TL-Software (Amersham Biosciences).

The following results were obtained:
Upregulation of the Cytosolic SOD-1 in Case of Keratinocytes
24 h:
Control: 18.2
Treated with glucosylglycerol solution: 85
96 h:
Control: 9.3
Treated with glucosylglycerol solution: 182
Upregulation of SOD-2 in Case of Fibroblasts
24 h:
Control: 16.5
Treated with glucosylglycerol solution: 419
96 h:
Control: 9.1
Treated with glucosylglycerol solution: 313

The invention claimed is:
1. A method of increasing expression of cell protective enzymes of a human having damaged skin and/or mucous membranes, for protection and stabilization of the human skin and/or mucous membranes, comprising administering to the human skin and/or mucous membranes glucosylglycerol and/or a glucosylglycerol ester so as to increase expression of a cell protective enzyme based on comparing the level of the cell protective enzyme before and after the administering, wherein the cell protective enzyme is a superoxide dismutase, and wherein the skin and mucous membranes are damaged by reactive oxygen compounds, free radicals, chemicals, toxins, allergens, denaturing substances, substances attaching to DNA, substances damaging or deactivating proteins, or airborne particulate.

2. The method according to claim 1, wherein the method is for the protection of human skin and/or mucous membrane against oxidative stress.

3. The method according to claim 2, wherein the method is for the protection of human skin and/or mucous membrane against reactive oxygen compounds or free radicals.

4. The method according to claim 1, wherein the method is for the protection of human skin and/or mucous membrane against chemicals, toxins, allergens, denaturing substances, substances attaching to DNA, substances damaging or deactivating proteins, or airborne particulate.

5. The method according to claim 1, characterized in that the glucosylglycerol is 2-O-α-D-glucosylglycerol.

6. The method according to claim 1, characterized in that the superoxide dismutase is SOD-1 or SOD-2.

7. The method according to claim 1, characterized in that the glucosylglycerol is provided in an aqueous solution.

8. The method according to claim 1, characterized in that concentration of glucosylglycerol ranges between 0.001% w/w and 10% w/w.

9. The method according to claim 8, characterized in that the concentration of glucosylglycerol ranges between 0.01% w/w and 6% w/w.

* * * * *